US008840160B2

(12) United States Patent
Caron L'Ecuyer et al.

(10) Patent No.: US 8,840,160 B2
(45) Date of Patent: Sep. 23, 2014

(54) MECHANICAL FINGER

(75) Inventors: Louis Joseph Caron L'Ecuyer, Montréal (CA); Charles Deguire, Boisbriand (CA)

(73) Assignee: Kinova, Montreal (CA)

( * ) Notice: Subject to any disclaimer, the term of this patent is extended or adjusted under 35 U.S.C. 154(b) by 12 days.

(21) Appl. No.: 13/377,600

(22) PCT Filed: Jun. 11, 2010

(86) PCT No.: PCT/CA2010/000910
§ 371 (c)(1),
(2), (4) Date: Mar. 29, 2012

(87) PCT Pub. No.: WO2010/142043
PCT Pub. Date: Dec. 16, 2010

(65) Prior Publication Data
US 2012/0185061 A1    Jul. 19, 2012

Related U.S. Application Data

(60) Provisional application No. 61/186,497, filed on Jun. 12, 2009, provisional application No. 61/227,511, filed on Jul. 22, 2009.

(51) Int. Cl.
*B66C 1/00* (2006.01)
*B25J 9/00* (2006.01)
*B25J 15/00* (2006.01)
*A61F 2/58* (2006.01)

(52) U.S. Cl.
CPC ............ *B25J 15/0009* (2013.01); *B25J 9/0009* (2013.01); *A61F 2/588* (2013.01); *A61F 2/586* (2013.01); *Y10S 901/39* (2013.01)
USPC ............................................. 294/106; 901/39

(58) Field of Classification Search
CPC ........ B25J 15/0009; B25J 15/08; B25J 15/10; B25J 1/02; A61F 2/586
USPC .......... 294/106, 115, 213; 623/64; 901/39, 38
See application file for complete search history.

(56) References Cited

U.S. PATENT DOCUMENTS 1,285,617 A * 11/1918 Caron ............................. 623/64
1,507,682 A *  9/1924 Pecorella et al. ............... 623/62
(Continued)

FOREIGN PATENT DOCUMENTS

DE       102006009559       5/2007
EP          1375087         1/2004

*Primary Examiner* — Saul Rodriguez
*Assistant Examiner* — Gabriela Puig
(74) *Attorney, Agent, or Firm* — Norton Rose Fulbright Canada LLP

(57) ABSTRACT

A mechanical finger comprises at least two phalanges. The phalanges have tubular bodies made of a semi-rigid material. One phalange is adapted to be secured to a base. Another phalange is connected to an adjacent phalange for pivoting movement with respect to the adjacent phalange. A skeleton member in the tubular bodies of the phalanges moves to actuate the pivoting motion of the phalanges with respect to one another. The skeleton member is connected to a degree of actuation to cause the pivoting motion of the phalanges with respect to one another. An assembly is also provided. The assembly comprises at least two of the mechanical finger, a palm actuator comprising a base for connection of the base phalange of each mechanical finger, and at least one degree of actuation connected to the skeleton member. The degree of actuation causes a grasping movement of the mechanical fingers.

20 Claims, 6 Drawing Sheets

(56) References Cited

U.S. PATENT DOCUMENTS

| | | | |
|---|---|---|---|
| 1,792,183 A * | 2/1931 | Pecorella | 623/64 |
| 2,493,776 A * | 1/1950 | Pecorella et al. | 623/64 |
| 2,553,827 A * | 5/1951 | Mason | 623/64 |
| 2,567,066 A | 9/1951 | Goldman | |
| 2,568,298 A * | 9/1951 | Philpott | 623/64 |
| 4,834,443 A * | 5/1989 | Crowder et al. | 294/106 |
| 5,762,390 A | 6/1998 | Gosselin | |
| 7,556,299 B2 * | 7/2009 | Koyama | 294/106 |
| 2007/0018470 A1* | 1/2007 | Hayakawa et al. | 294/106 |
| 2009/0015026 A1* | 1/2009 | Matsuda et al. | 294/106 |
| 2011/0156416 A1* | 6/2011 | Kawanami et al. | 294/110.1 |

* cited by examiner

MECHANICAL FINGER

CROSS-REFERENCE TO RELATED APPLICATION(S)

The present application is a U.S. national stage of International Patent Appliocation No. PCT/CA2010/00910. The present application claims the benefit of U.S. Patent Application No. 61/186,497, filed Jun. 12, 2010, and U.S. Patent Application No. 61/227,511, filed Jul. 22, 2009, and incorporated herein by reference.

FIELD OF THE APPLICATION

The present application relates to mechanical fingers and more particularly to mechanical fingers used in prosthesis applications and in technical-aid applications, amongst numerous possible applications.

BACKGROUND OF THE ART

Mechanical fingers of all types have been developed as a function of various applications. One common type of mechanical finger has phalanges in an articulated configuration, to simulate the human finger. In such configurations, the articulated phalanges are displaced with respect to one another to grasp objects of all shapes. For instance, U.S. Pat. No. 5,762,390, by Gosselin et al., describes a mechanical finger performing motions similar to that of the human finger. Accordingly, a set of mechanical fingers of Gosselin et al. can be used to perform actions such as a pinch grasps. The mechanical finger taught by Gosselin et al. is more practical in industrial applications. The mechanical finger of Gosselin et al. is made of rigid phalanges that can support substantial weights. In domestic applications, such a mechanical finger may be impractical, especially in an environment with relatively fragile objects.

SUMMARY OF THE APPLICATION

It is therefore an aim of the present disclosure to provide a mechanical finger that addresses issues associated with the prior art.

It is a further aim of the present disclosure to provide a mechanical finger of semi-rigid material.

Therefore, in accordance with a first embodiment, there is provided a mechanical finger comprising: at least two phalanges, with the at least two phalanges having tubular bodies and being made of a semi-rigid material, one of the at least two phalanges being a base phalange adapted to be secured to a base; another of the at least two phalanges being an end phalange, the end phalange being pivotally connected to an adjacent one of the at least two phalanges for pivoting movement with respect to the adjacent one of the at least two phalanges; and a skeleton member received in the tubular bodies of the at least two phalanges and movable to actuate the pivoting motion of the at least two phalanges with respect to one another, the skeleton member adapted to be connected to a degree of actuation for causing the pivoting motion of the at least two phalanges with respect to one another.

Further in accordance with the first embodiment, the mechanical finger comprises three of the phalanges, with one of the three phalanges being a middle phalange pivotally connected to the base phalange at a first end, and pivotally connected to the end phalange at a second end.

Still further in accordance with the first embodiment, at least a pair of shells are interconnected to define the tubular bodies of the at least two phalanges.

Still further in accordance with the first embodiment, two of the shells are interconnected along a longitudinal plane of the mechanical finger, each of the two shells comprising half-phalanges pivotally interconnected, whereby the half-phalanges define the at least two phalanges when the shells are interconnected.

Still further in accordance with the first embodiment, the two shells are mirror images one of the other, and each are one integrally molded piece.

Still further in accordance with the first embodiment, each of the shells comprises a longitudinal edge ridge, with a slit defined in the longitudinal edge ridge between each adjacent pair of the at least two phalanges to form a pivot between the adjacent pair of phalanges when the shells are interconnected.

Still further in accordance with the first embodiment, a tail of material extends from one of the phalanges into a tubular body of an adjacent other phalanges opposite the pivot, the tail covering an interior of the tubular body when the phalanges are pivoted with respect to one another.

Still further in accordance with the first embodiment, the mechanical finger comprises one said tail of material between each pair of adjacent phalanges of the mechanical finger.

Still further in accordance with the first embodiment, the mechanical finger comprises a peripheral flange at an end of the base phalange adapted to be connected to a base, with slots in the peripheral flange adapted to receive fasteners.

Still further in accordance with the first embodiment, the skeleton member comprises an articulated arm extending into the tubular bodies of the at least two phalanges and interconnected to at least one of the at least two phalanges.

Still further in accordance with the first embodiment, the articulated arm has at least two arm segments, with each interconnected pair of the arm segments being separated by a throat portion forming a pivot connected between the arm segments of each interconnected pair.

Still further in accordance with the first embodiment, an actuator end of the articulated arm has an annular body adapted to be connected to the degree of actuation.

Still further in accordance with the first embodiment, the annular body is tapped for screwingly engaging with the degree of actuation.

Still further in accordance with the first embodiment, the annular body extends outside of the tubular bodies of the at least two phalanges.

Still further in accordance with the first embodiment, the articulated arm has an end pivot at an end thereof, further wherein the tubular bodies have a pivot housing for rotatably receiving the end pivot whereby an actuation of the skeleton member causes a rotation of the end pivot with respect to the pivot housing.

Still further in accordance with the first embodiment, abutment walls are adjacent to the pivot housing for delimiting a rotational movement of the articulated arm with respect to the pivot housing.

Still further in accordance with the first embodiment, the pivot housing is in the end phalange, and the mechanical finger further comprises a middle pivot on the articulated arm and a pivot slot in the tubular bodies for rotatably and slidingly receiving the middle pivot for transmission of the actuation of the skeleton member to the middle phalange.

Still further in accordance with the first embodiment, the mechanical finger comprises at least a biasing member in the tubular bodies and interconnected between the skeleton member and the at least two phalanges to bias the mechanical finger in one orientation.

Still further in accordance with the first embodiment, the skeleton member is one integrally molded piece.

Still further in accordance with the first embodiment, the skeleton member is entirely made of a semi-rigid material, whereby the mechanical finger is compliant isotropically.

Still further in accordance with the first embodiment, the skeleton member is made of a semi-rigid material, with rigid reinforcements thereon.

In accordance with a second embodiment, there is provided an assembly comprising: at least two of the mechanical finger according to the first embodiment; a palm actuator comprising a base for connection of the base phalange of each of the at least two mechanical fingers; and at least one degree of actuation connected to the skeleton member of the mechanical fingers for simultaneously causing a grasping movement of the mechanical fingers.

Further in accordance with the second embodiment, the assembly comprises a single one of the degree of actuation and three of the mechanical finger, with the single one of the degree of actuation simultaneously actuating all three of the mechanical fingers.

DESCRIPTION OF PREFERRED EMBODIMENTS

Figure 1:
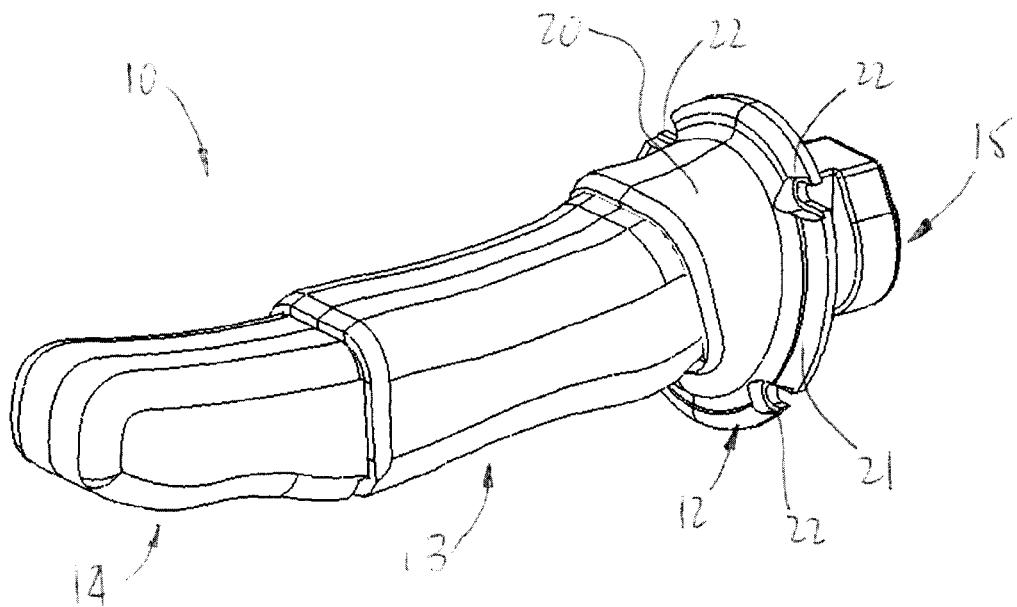
FIG. 1 is a perspective view of a mechanical finger constructed in accordance with an embodiment of the present disclosure.

Referring to the drawings, and more particularly to FIG. 1, a mechanical finger constructed in accordance with an embodiment is generally shown at 10. The finger 10 has a base phalange 12, a middle phalange 13 and an end phalange 14, although more or fewer than three phalanges may be used in the mechanical finger of the present disclosure. The three-phalange configuration illustrated in FIG. 1 is however well suited to simulate a human finger, whereby the present disclosure will focus on the three-phalange configuration. Movements of the mechanical finger 10 are performed by actuation of a skeleton member 15.

Figure 2:
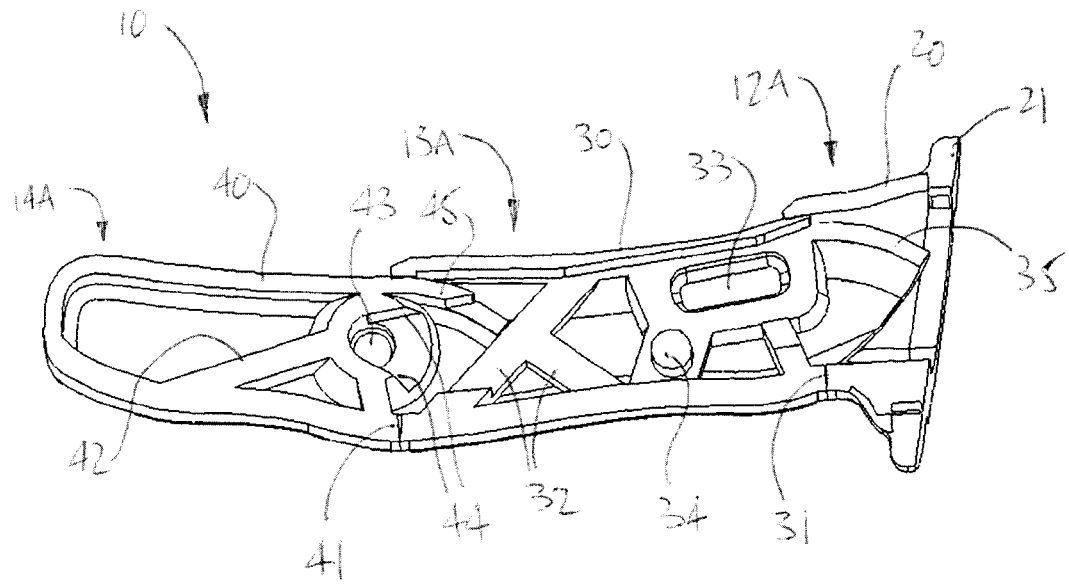
FIG. 2 is a perspective view of the mechanical finger of FIG. 1, with a half shell of the mechanical finger removed to show an interior of the mechanical finger.

Referring concurrently to FIGS. 1 and 2, the phalanges 12-14 of the mechanical finger 10 each consist in a pair of shells made of a semi-rigid material, such as rubber, as will be described hereinafter. In FIG. 2, half-phalanges are shown as 12A, 13A and 14A (i.e., first shells), with the plane of separation being parallel to a longitudinal axis of the finger 10. The removed half-phalanges (i.e., second shells) are typically a mirror image of the half-phalanges 12A-14A illustrated in FIG. 2.

The base phalange 12 has a tubular body 20, at the base of which a peripheral flange 21 is provided. The flange 21 has connection slots 22, for the base phalange 12 to be connected to a palm or actuator using fasteners such as bolts. Counterbore holes may be used amongst other possibilities.

The middle phalange 13 also has a tubular body 30, with a diameter lesser than that of the base phalange 12, such that the middle phalange 13 has an end partially accommodated in the base phalange 12. The tubular body 30 is hinged to the tubular body 20 by slit 31. The slit 31 is essentially a disruption in the thickness of ridges forming a periphery of the shells of the bodies 20 and 30. As the bodies 20 and 30 are made of a semi-rigid material, the slit 31 will facilitate deformation thereat, and hence will allow a hinging movement of the middle phalange 13 with respect to the base phalange 12. Other configurations are considered as well, such as the insertion of a pivot, as alternatives to the narrowing of the material.

The tubular body 30 has strengthening ribs 32, to increase the structural integrity of the middle phalange 13. A slot 33 is defined in each shell of the middle phalange 13, to form a translational joint with the skeleton member 15, as will be described hereinafter. A post 34 is also provided within the tubular body 30. When the shells 13A are interconnected to form the phalange 13, the posts 34 abut against one another and therefore define a connection point for a resilient member such as a spring, as will be shown hereinafter. The tubular body 30 also features a tail 35, accommodated in the tubular body 20. The tail 35 ensures that an interior of the finger 10 is not exposed when the middle phalange 13 is pivoted away from the base phalange 12, for instance as shown in FIG. 5B.

Still referring to FIGS. 1 and 2, the end phalange 14 also has a tubular body 40, forming the tip of the mechanical finger 10. The tubular body 40 has a diameter lesser than that of the middle phalange 13, such that the end phalange 14 has an end partially accommodated in the middle phalange 13. The tubular body 40 is hinged to the tubular body 30 by slit 41. Similar to the slit 31, the slit 41 is essentially a disruption in the thickness of the ridges defining a periphery of the shells of the bodies 30 and 40. As the bodies 30 and 40 are made of a semi-rigid material, the slit 41 will facilitate deformation thereat, and hence will allow a hinging movement of the end phalange 14 with respect to the middle phalange 13. Other configurations are considered as well, such as the insertion of a pivot, as an alternative to the narrowing of the material.

The tubular body 40 has strengthening ribs 42, to increase the structural integrity of the end phalange 14. Moreover, the tubular body 40 has a pair of pivot housings 43 (one in each shell), that will rotatably receive an end of the skeleton member 15. A pair of abutment walls 44 are positioned adjacent to each pivot housing 43 to delimit movement of the end phalange 14 with respect to the skeleton member 15. The tubular body 40 also features a tail 45, accommodated in the tubular body 30. The tail 45 ensures that an interior of the finger 10 is not exposed when the end phalange 14 is pivoted away from the middle phalange 13.

The mechanical finger 10 of FIGS. 1 and 2 has the shells 12A-14A of the phalanges 12-14 molded integrally in one piece, with the narrowing of material allowing the pivoting movement between the phalanges. Alternatively, the phalanges 12-14 may be separate components, for instance interconnected by rigid pivot pins. Accordingly, in the embodiment of FIGS. 1 and 2, the two half-fingers (each made up of the interconnected shells 12A-14A) are connected together to form the full finger of FIG. 1, with the skeleton member 15 inserted therein. Mating connectors (not shown), adhesives, or the like may be used to maintain the half-fingers together.

Moreover, the construction of the mechanical finger 10 as described above may cause a generally isotropic flexibility of the finger 10, for instance in all directions. Alternatively, reinforcements may be used to render the flexibility anisotropic. The flexibility is due to the use of the semi-rigid material. Moreover, the use of tubular bodies for the phalanges 12-14 also allows some flexibility. Although the shells 12A-14A are shown having a relatively thin wall thickness, it is considered to have relatively solid shells 12A-14A, with a passage for the skeleton member (hence the expression tubular bodies).

Figure 3:
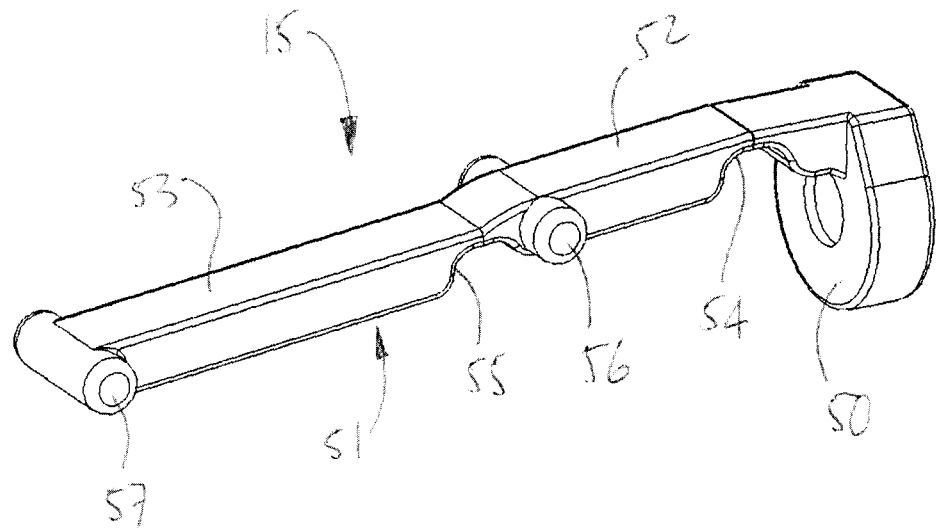
FIG. 3 is a perspective view of the skeleton member of the mechanical finger of FIG. 1.

Referring to FIG. 3, the skeleton member 15 has an actuator end 50, and an elongated articulated arm 51 projecting from the actuator end 50. The actuator end 50 may be of any shape as a function of the actuator used with the mechanical finger 10. In FIG. 3, the actuator end 50 has an annular shape to be connected to an output rod of an endless screw actuator. The inner surface of the actuator end 50 may therefore be tapped to move in translation as a function of a rotation from the endless screw. The annular shape of the actuator end 50 is also well suited for connection with a rod or shaft of a translational actuator.

The articulated arm 51 has a first arm segment 52 and a second arm segment 53. The first arm segment 52 is connected to the actuator end 50 by a first throat portion 54, whereas the arm segments 52 and 53 are interconnected by a second throat portion 55. The throat portions 54 and 55 are essentially narrowing locations in the articulated arm 51, allowing the pivoting movement between interconnected parts. A flaring shape of the throat portions 54 and 55 ensures that the skeleton member 15 bends in the direction shown for instance in FIGS. 5A-5D, when actuated. Alternative constructions are considered as well, such as the use of pivot pins for separated components. However, the articulated arm 51 of FIG. 3 is an integrally molded piece.

Figure 4:
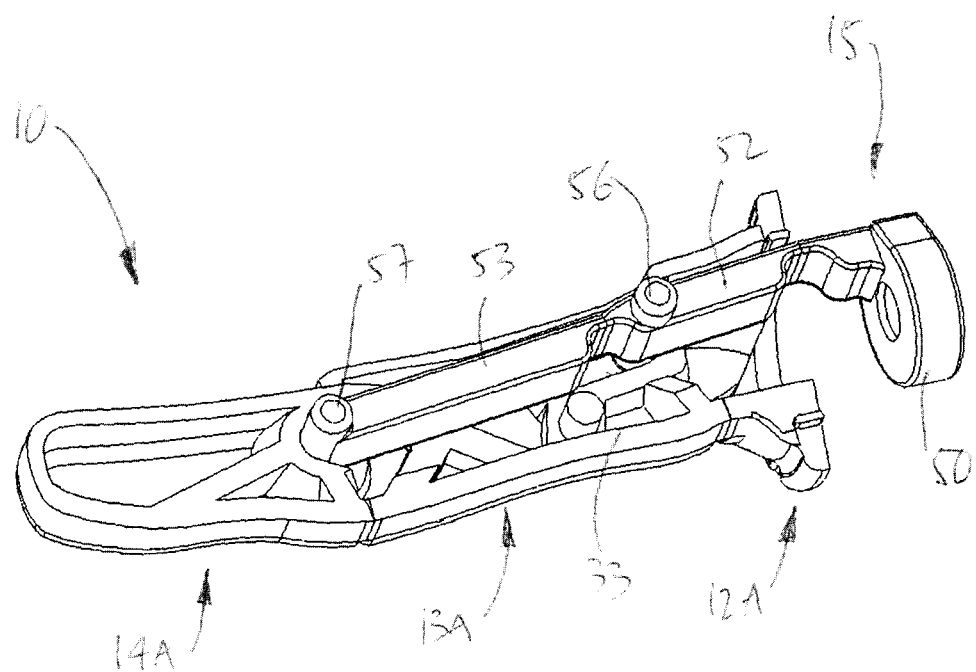
FIG. 4 is a perspective view of the skeleton member of FIG. 3 in the half shell of FIG. 2.

Referring concurrently to FIGS. 3 and 4, follower 56 is provided on the first arm segment 52, adjacent to the throat portion 54. The ends of the follower 56 are received in the slots 33 (one shown) in the middle phalange 13, thereby forming a translational/rotational joint. Accordingly, a translational movement of the actuator end 50 may result in a translational movement of the follower 56 in the slots 33, and/or a rotation of the middle phalange 13 with respect to the base phalange 12, when the follower 56 abuts against the ends of the slots 33.

Pivot 57 is positioned on the second arm segment 53, and received in the pivot housings 43 (one shown) in the end phalange 14. Therefore, a translational movement of the actuator end 50 will result in a pivoting movement of the end phalange 14 with respect to the pivot 57, and hence with respect to the middle phalange 13.

According to an embodiment, the skeleton member 15 is made of a combination of semi-rigid material and rigid reinforcements (e.g., metal, plastic, etc). For instance, the skeleton member 15 may be a molded integral piece in the semi-rigid material, with rigid reinforcement plates on the arm segments 52 and 53, and caps or the like on the follower 56 and the pivots 57. As they are on portions of the skeleton member 15, rigid reinforcements do not substantially affect the flexibility of the mechanical finger 10.

Figure 5A:
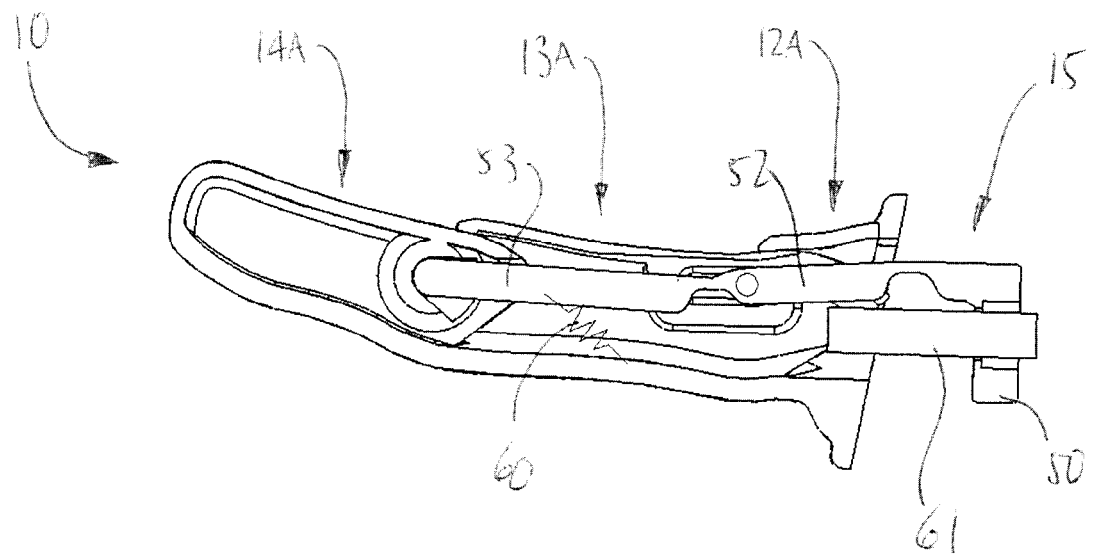
FIG. 5A to 5D shows sequences of the assembly of FIG. 4 as actuated in a grasping movement, with and without contact with an object.
Figure 5B:
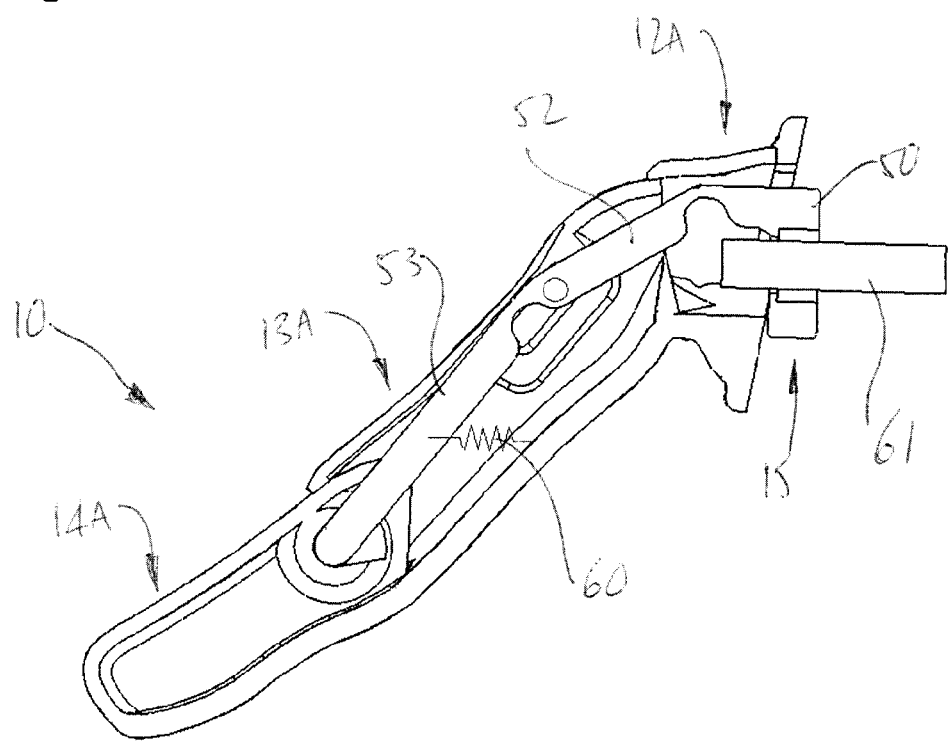

Referring to FIGS. 5A-5D, a sequence of grasping movements of the finger 10 is illustrated, without and with contact against an object X. In FIGS. 5A-5D, a compression spring 60 is provided in the mechanical finger 10, between the skeleton member 15 and an interior of the middle phalange 13. Although a coil spring is illustrated, any other suitable type of resilient member can be used. The compression spring 60 maintains the end phalange 14 straight with respect to the middle phalange 13, in the absence of an exterior restriction. In FIG. 5A, the actuator end 50 of the skeleton member 15 is at a first position along the endless screw shaft 61 of an actuator. In this first position, the skeleton member 15 is generally straight, resulting in the phalanges 12-14 of the finger 10 being in a straight relation with respect to one another.

In FIG. 5B, the actuator end 50 has moved along the endless screw shaft 61 to a second position, as a result of a rotation of the endless screw shaft 61. Because of the compression spring 60 keeping the phalanges 13 and 14 in a straight relation, it is the arm segment 52 that has pivoted with respect to the actuator end 50, resulting in the bending of the middle phalange 13 with respect to the base phalange 12.

Figure 5C:
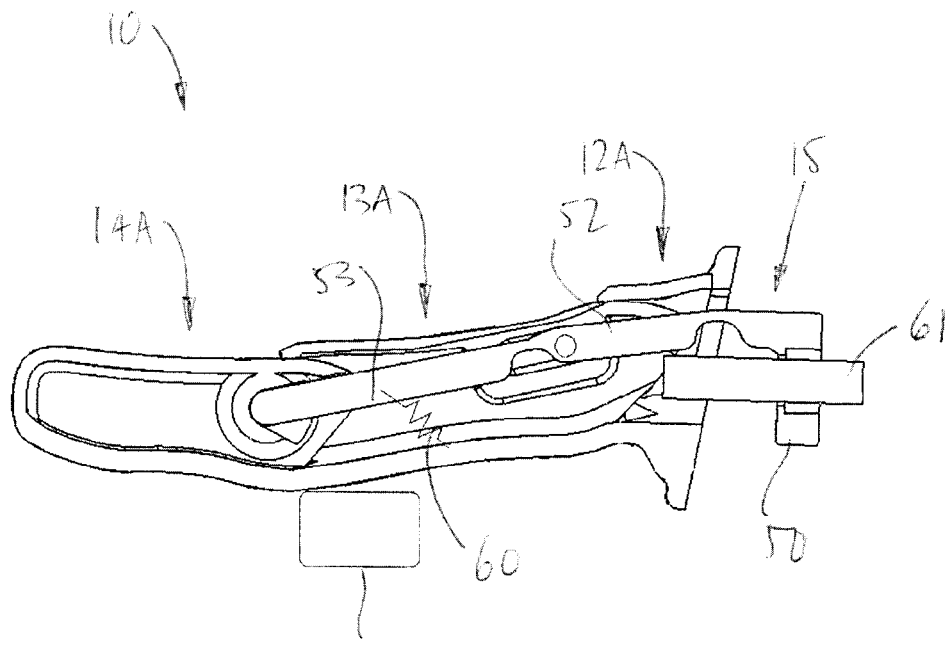
Figure 5D:
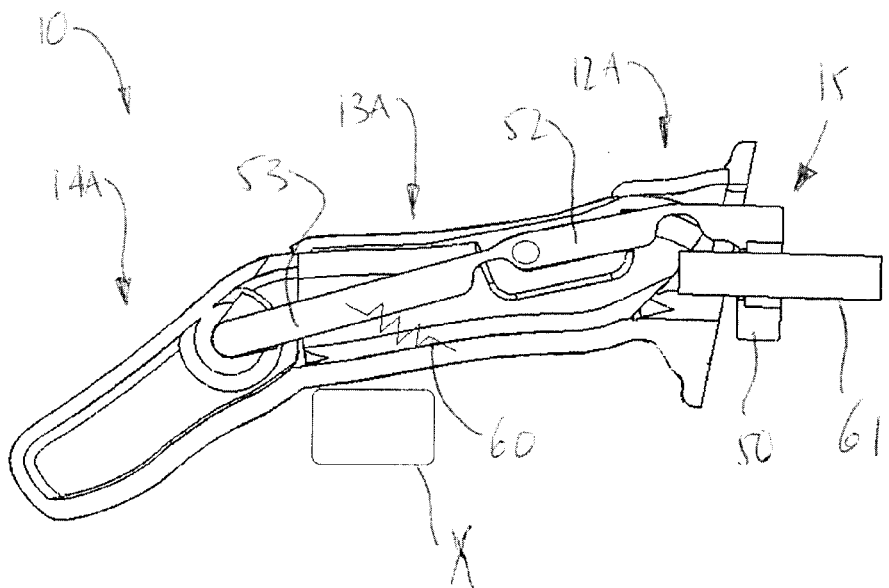

Referring to FIGS. 5C-5D, the actuator end 50 is in the same two positions along the shaft 61 as in FIGS. 5A and 5B, but with an object X abutting against the middle phalange 13. The object X prevents the bending of the middle phalange 13 with respect to the base phalange 12. Accordingly, the translation of the articulated arm 51 of the skeleton member 15 pushes the end phalange 14 into pivoting with respect to the middle phalange 13, against the action of the compression spring 60. The finger 10 in combination with other fingers 10 may therefore grasp the object. In the sequence of FIGS. 5C and 5D, the follower 56 has moved in translation in the slot.

In FIGS. 5A-5D, it is observed that the base phalange 12 has not moved. This is due to the fact the base phalange 12 is anchored to an actuator casing or palm, not shown for clarity purposes.

Figure 6:
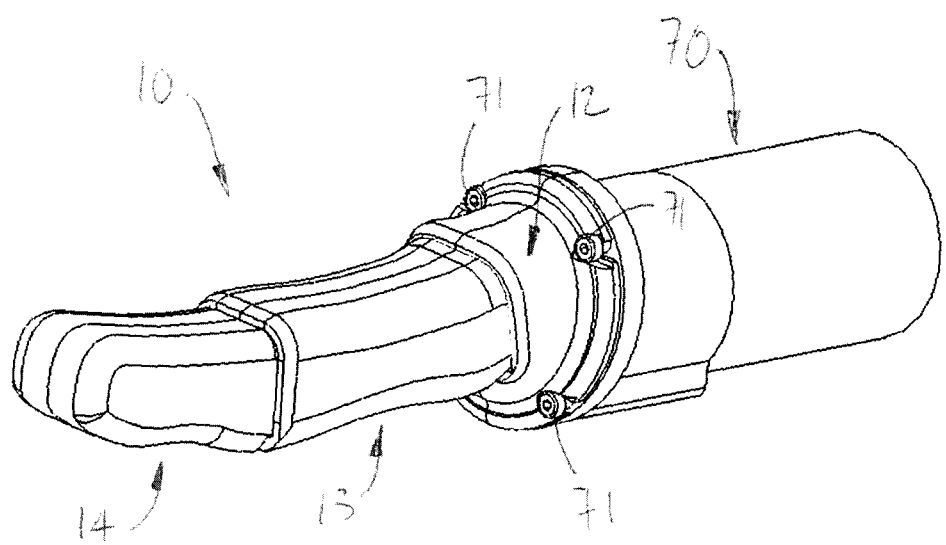
FIG. 6 is a perspective view of the mechanical finger of FIG. 1, as mounted to a single actuator.

Referring to FIG. 6, the mechanical finger 10 is secured to an actuator 70. The actuator 70 may be a endless screw actuator as described previously, or any other actuator directing the actuator end 50 (FIG. 3) in a translational movement. Bolts 71 anchor the base phalange 12 to a casing of the actuator 70, by being received in the connection slots 22.

Figure 7:
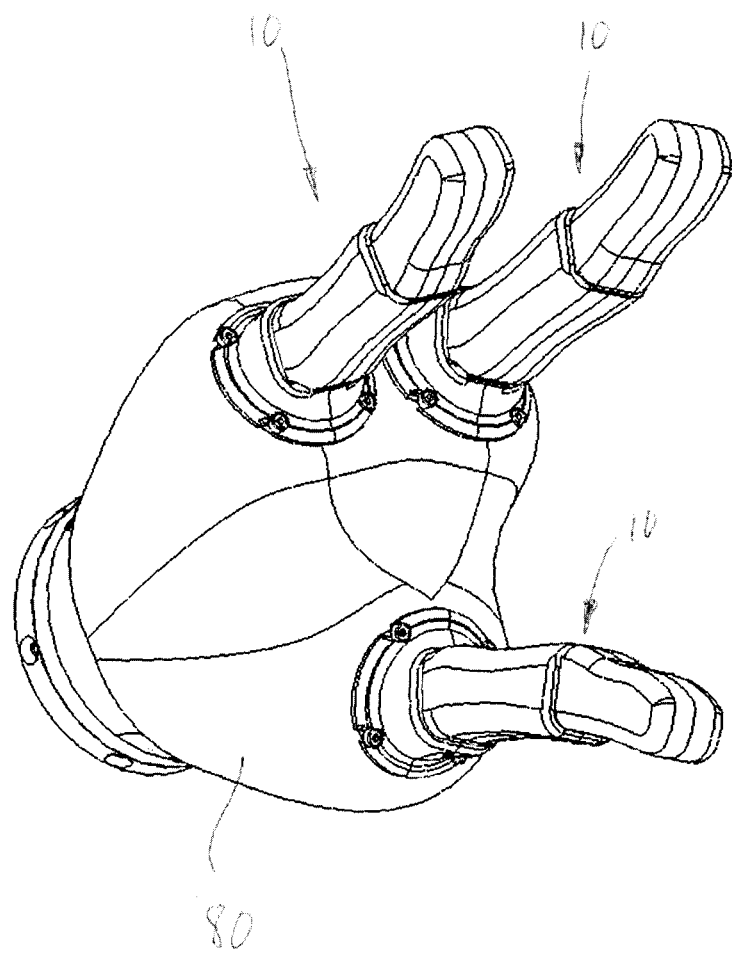
FIG. 7 is a perspective view of the mechanical finger of FIG. 1, as mounted to a palm actuator.

Referring to FIG. 7, three of the mechanical finger 10 are mounted to a palm actuator 80. The palm actuator 80 provides actuation to all three of the mechanical fingers 10 in the manner described above. Although not shown, it is considered to provide the palm actuator 80 with orientation actuation, so as to orient the fingers 10 in view of specific tasks (e.g., pinch grasp). The fingers 10 of the palm actuator 80 may be interrelated such that the single degree of actuation of the palm actuator 80 produces the actuation of each mechanical finger 10, making the combination of the mechanical fingers 10 and palm actuator 80 underactuated. This interrelation may be achieved by having a transmission connected to the input shaft of the palm actuator 80, which transmission has multiple output shafts connected to the actuator ends 50 of all skeleton members 15.

As discussed above, the phalanges 12-14 and the skeleton member 15 are preferably made of a semi-rigid material, whereby all structural members are made of the semi-rigid material, making the mechanical finger compliant in all directions in case of contacts causing a force of a given magnitude. For instance, these components are molded in a polymeric material or rubber having a hardness ranging between 50 and 98 Shore A, although a hardness outside of the range may be used as well. The hardness of the components is selected as a function of the application of the mechanical finger 10. As an alternative to having the skeleton member 15 being made of the same or a similar material as the phalanges 12-14, it is considered to fabricate the skeleton member 15 in a rigid material (e.g., metal), or to use cables or the like as skeleton member.

The shells of the phalanges 12-14 may be molded with gripping patterns, such as a knurling pattern, on the contact areas of the phalanges 12-14. Such gripping patterns increase the friction surface at the contact areas.

Although the mechanical finger 10 is well suited for prosthesis and technical-aid applications, it is pointed out that the mechanical finger 10 may be used for any other appropriate application. For instance, robots or manipulators may be equipped with the mechanical finger 10 in white-room applications, to manipulate chemicals. This is one application among numerous others.

The invention claimed is:

1. A mechanical finger comprising:
    at least two phalanges, with the at least two phalanges each made of a semi-rigid material forming a tubular body, one of the at least two phalanges being a base phalange adapted to be secured to a base;
    another of the at least two phalanges being an end phalange, the end phalange being pivotally connected to an adjacent one of the at least two phalanges for pivoting movement with respect to the adjacent one of the at least two phalanges;
    a skeleton member received in the tubular bodies of the at least two phalanges and movable to actuate the pivoting motion of the at least two phalanges with respect to one another, the skeleton member adapted to be connected to a degree of actuation for causing the pivoting motion of the at least two phalanges with respect to one another; and
    a degree of flexibility in all directions for the assembly of at least two phalanges and skeleton member therein, whereby the mechanical finger is compliant in all said directions.

2. The mechanical finger according to claim 1, further comprising three of the phalanges, with one of the three phalanges being a middle phalange pivotally connected to the base phalange at a first end, and pivotally connected to the end phalange at a second end.

3. The mechanical finger according to claim 2, wherein the skeleton member comprises an articulated arm extending into the tubular bodies of the at least two phalanges and interconnected to at least one of the at least two phalanges.

4. The mechanical finger according to claim 3, wherein the articulated arm has at least two arm segments, with each interconnected pair of the arm segments being separated by a throat portion forming a pivot connected between the arm segments of each interconnected pair.

5. The mechanical finger according to claim 3, wherein an actuator end of the articulated arm has an annular body adapted to be connected to the degree of actuation.

6. The mechanical finger according to claim 5, wherein the annular body extends outside of the tubular bodies of the at least two phalanges.

7. The mechanical finger according to claim 3, wherein the articulated arm has an end pivot at an end thereof, further wherein the tubular bodies have a pivot housing for rotatably receiving the end pivot whereby an actuation of the skeleton member causes a rotation of the end pivot with respect to the pivot housing.

8. The mechanical finger according to claim 7, further comprising abutment walls adjacent to the pivot housing for delimiting a rotational movement of the articulated arm with respect to the pivot housing.

9. The mechanical finger according to claim 1, comprising at least a pair of shells interconnected to define the tubular bodies of the at least two phalanges.

10. The mechanical finger according to claim 9, comprising two of the shells interconnected along a longitudinal plane of the mechanical finger, each of the two shells comprising half-phalanges pivotally interconnected, whereby the half-phalanges define the at least two phalanges when the shells are interconnected.

11. The mechanical finger according to claim 10, wherein the two shells are mirror images one of the other, and each are one integrally molded piece.

12. The mechanical finger according to claim 10, wherein each of the shells comprises a longitudinal edge ridge, with a slit defined in the longitudinal edge ridge between each adjacent pair of the at least two phalanges to form a pivot between the adjacent pair of phalanges when the shells are interconnected.

13. The mechanical finger according to claim 1, further comprising a tail of material extending from one of the phalanges into a tubular body of an adjacent other phalanges opposite the pivot, the tail covering an interior of the tubular body when the phalanges are pivoted with respect to one another.

14. The mechanical finger according to claim 13, comprising one said tail of material between each pair of adjacent phalanges of the mechanical finger.

15. The mechanical finger according to claim 1, further comprising a peripheral flange at an end of the base phalange adapted to be connected to a base, with slots in the peripheral flange adapted to receive fasteners.

16. The mechanical finger according to claim 1, wherein the skeleton member is one integrally molded piece.

17. The mechanical finger according to claim 1, wherein the skeleton member is entirely made of a semi-rigid material, whereby the mechanical finger is compliant isotropically.

18. The mechanical finger according to claim 1, wherein the skeleton member is made of a semi-rigid material having a hardness ranging between 50 and 98 Shore A.

19. The mechanical finger according to claim 1, further comprising at least a biasing member in the tubular bodies and interconnected between the skeleton member and the at least two phalanges to bias the mechanical finger in one orientation.

20. The mechanical finger according to claim 1, wherein the degree of flexibility is generally isotropic in all directions.

* * * * *